United States Patent [19]
Cordon

[11] Patent Number: 5,473,966
[45] Date of Patent: Dec. 12, 1995

[54] METHOD FOR SIZING TRANSDERMAL PATCH

[75] Inventor: Moraima Cordon, Redwood City, Calif.

[73] Assignee: Pulmonary Diagnostic & Rehabilitation Medical Group, Inc., Palo Alto, Calif.

[21] Appl. No.: 189,373

[22] Filed: Jan. 31, 1994

[51] Int. Cl.[6] ....................................... B26D 3/00
[52] U.S. Cl. ............................ 83/56; 83/821; 33/563
[58] Field of Search ............................... 83/13, 56, 821; 33/562, 563, 566, 567

[56] References Cited

U.S. PATENT DOCUMENTS

| 697,701 | 4/1902 | Ayer | 33/562 |
|---|---|---|---|
| 3,961,552 | 6/1976 | Graham | 83/821 |
| 5,238,933 | 8/1993 | Catz et al. | 514/236.2 |

*Primary Examiner*—Richard K. Seidel
*Assistant Examiner*—Raymond D. Woods
*Attorney, Agent, or Firm*—Townsend and Townsend and Crew

[57] ABSTRACT

A device and method for reducing the area of a transdermal patch without altering its pharmacokinetic profile are provided. The area of a transdermal patch is reduced by aligning the patch at a location on a template which uniquely matches a dimension of the patch. The patch is then cut along a line defined by an edge of the template when the patch is at the aligned location. The template can be selected from a group of templates which correspond to the desired percentage of area reduction of the patch. A sizing template for proportionally reducing the size of a transdermal patch which is one of a group of orthogonal patches of differing sizes is also provided. The template comprises a planar member having a straight bottom edge and a stepped top edge. The width of each step on the top edge is configured to uniquely match the width of one of the transdermal patches in the group. The height of the step defines a cutting line on which the patch is to be cut to achieve a preselected percentage of size reduction.

10 Claims, 3 Drawing Sheets

METHOD FOR SIZING TRANSDERMAL PATCH

BACKGROUND OF THE INVENTION

1. Field of the Invention

The present invention relates to a device and method for reducing the area of a transdermal patch. More specifically, the invention provides a sizing template used to reduce the area of a transdermal patch by a desired percentage.

A transdermal patch is a patch containing a drug that, when applied to the skin, delivers the drug through the skin to the patient. Although the concept appears simple, the method of transferring a drug through the skin via a transdermal patch is quite complex. Even so, transdermal patches are currently used for delivering numerous drugs, including nitroglycerine, isosorbide dinitrate, scopolamine, clonidine, progesterone, estradial, nicotine, and fentanyl. Of particular interest to the present invention are nicotine transdermal patches used for delivering nicotine in connection with therapy for smoking cessation.

Several types of transdermal patch designs are now in commercial use. A summary of these designs is given in Gary W. Cleary, "Transdermal Drug Delivery," *Cosmetics and Toiletries,* May 1991, which is herein incorporated by reference. Of particular importance to the present invention are transdermal patches having a "solid-state" design where each patch has a defined surface area, and the amount of drug delivered to the patient corresponds to the surface area of the patch. Solid-state design also allows the patches to be cut into smaller patches without altering the pharmacokinetic delivery profile, i.e. amount of drug delivered per unit area. Examples of patches with solid-state designs are Nicotrol®, manufactured by Cygnus Therapeutic Systems, supplied by Kabi Pharmacia AB, and distributed by Parke-Davis, and Nicoderm®, distributed by Marion Merril Dow.

The use of solid-state design patches is thus advantageous when used in connection with a therapeutic system where the patient must have either tailored dosages or tapered dosages of the prescribed drug. Tailoring the dosage of the prescribed drug can be accomplished by using a number of differently sized patches singly or in combination to ensure the patient receives the appropriate amount of drug. While patches will often be available in at least several sizes, the patches needed to obtain the prescribed dosage will often differ from the available sizes. In such cases the required surface area may be obtained by cutting the patch to reduce its surface area by a desired percentage, where the delivered drug dosage is reduced by the same percentage.

One problem that can occur with either tailoring or tapering in the manner just described is that the patches may be cut to an incorrect size. This will typically occur when a patient, without proper assistance from medical personnel, tries to reduce or alter the size of the patch. While it would be possible for the patient to visit the doctor's office to have the patches cut, such visits will be inconvenient to the patient and inefficient for the doctor.

A desired solution to such a problem is to provide a template to enable a patient to cut a single sized patch from a larger commercially available patch to obtain the necessary patch size as prescribed by the doctor. However, a template designed only to reduce one size of patch would be incompatible for use with commercially available patches which are available in a number of various patch sizes. Further, if a patient were given such a template by the doctor with instructions to reduce the area of one particular sized patch to be used in combination with another (original sized) patch to obtain the necessary dosage, the patient would have difficulty in determining which size of patch the template was to be used with. In such a case, the patient may mistakenly use the template to cut the patch that was not intended to be cut, while the patch that was to be reduced in size was not. Even if the template indicated which size of patch were to be cut, the patient would still have difficulty in determining the correct patch to be cut because commercially available patches are not typically marked with a size indication.

A method and a device are therefore needed to simply and easily reduce the area of a transdermal patch to allow a patient to either tailor or taper their dosage of the prescribed drug within the patch. The method and device should be economical for the patient so that the patient may use only one prescribed set of patches without having to purchase new patches of differing sizes for each different prescribed dosage.

2. Description of the Background Art

U.S. Pat. No. 1,827,375 describes a template to position an address on letter head to ensure that, when folded an inserted into an envelope, the address will be visible through a window in the envelope.

U.S. Pat. No. 1,624,150 describes a gauge used to measure the thickness of a piece of lumber.

U.S. Pat. No. 1,380,187 describes a measuring and gauging device particularly useful for dressmakers. One use of the device is for gauging the evenness of the hang of a skirt.

U.S. Pat. No. 2,834,522 describes a tool for manually forming pleats for clothing.

U.S. Pat. No. 4,736,525 describes a floor square for use in squaring and marking a ledger notch in the end of a floor joist and for use in marking the intended position of a ledger on a girder.

U.S. Pat. No. 4,266,388 describes a template for positioning an array of overlapping shingles on a roof.

U.S. Pat. No. 2,981,005 shows a bolt gauge to measure bolt diameters and lengths.

U.S. Pat. No. 3,201,873 describes a gauge block with a graduated stepped gauging edge for engagement with a mating part of a machine such as a saw or router to establish a desired dimension.

Popular Science, 20-IN-1 Shop Guide, ©1966 shows a "shop" template used to measure the length and diameter of screws, nuts, bolts, drill bits, nails, etc.

SUMMARY OF THE INVENTION

A device and a method for reducing the area of a transdermal patch which is one of a group of orthogonal patches of different sizes are provided. According to one method, the area of a transdermal patch is reduced by aligning the patch at a location on a template which uniquely matches a dimension of the patch. By "unique", it is meant that the dimension of the template distinguishes that size of patch from differently sized patches of the same group. The template will have one unique location for each size of patch and will provide an edge which is positioned to define a line along which the patch may be cut to reduce its area by a desired and a specific percentage. The patch is then cut along the line defined by the template to reduce patch dosage by a desired percentage. The method further provides for selecting the template from a group of templates which correspond to different size reduction percentages. If desired, the transdermal patch can be marked along the line defined by the template prior to cutting to enable a user to remove the template before cutting the patch. Alternatively, the patch can be cut while aligned with the template by axially translating a sharp instrument along the line defined by an edge of the template.

A sizing template for proportionally reducing the size of a transdermal patch which is one of a group of orthogonal patches of differing sizes is also provided. The template comprises a planar member having a straight bottom edge and a stepped top edge. The width of each step on the top edge is configured to uniquely match the width of one of the orthogonal transdermal patches in the group. The top edge of the step defines a cutting line on which the patch is to be cut to achieve a preselected percentage of size reduction. The template can also be constructed to have a desired thickness to enable a marking or severing instrument to be axially translated along the stepped edge to either mark or cut the patch. Preferably, the template will be substantially rigid, and will be constructed from polycarbonate, cardboard, cardstock, plastic laminated cardstock, paper stock, plastics, metals, or the like. In one embodiment, the steps of the stepped top edge are configured in an ascending or descending order.

A further understanding of the nature and advantages of the invention will become apparent by reference to the remaining portions of the specification and drawings.

DETAILED DESCRIPTION OF SPECIFIC EMBODIMENTS

The present invention provides a device and method for reducing the area (and resulting dosage) of a transdermal patch. Transdermal patches which are particularly suitable for use with the present invention include patches that may be cut to reduce their size without altering the pharmacokinetic delivery profile of the patch. Typically, transdermal patches that fall into this category include true solid-state design patches, such as Type IVa, Type IVb, and Type IVc patches as set forth in Gary W. Cleary, "Transdermal Drug Delivery," *Cosmetics and Toiletries*, May 1991, already incorporated herein by reference.

Drug candidates amenable to the present invention include all those which may be delivered by solid-state patches, such as nicotine, nitroglycerins, isosorbide dinitrate, scopolamine, clonidine, progesterone, estradial, fentanyl, and the like. Of particular importance to the present invention are nicotine transdermal patches; particularly, Nicotrol®, manufactured by Cygnus Therapeutic Systems, supplied by Kabi Pharmacia AB, and distributed by Parke-Davis, and Nicoderm®, distributed by Marion Merril Dow, both of which are solid-state patches and are typically used in connection with smoking cessation.

Figure 1:
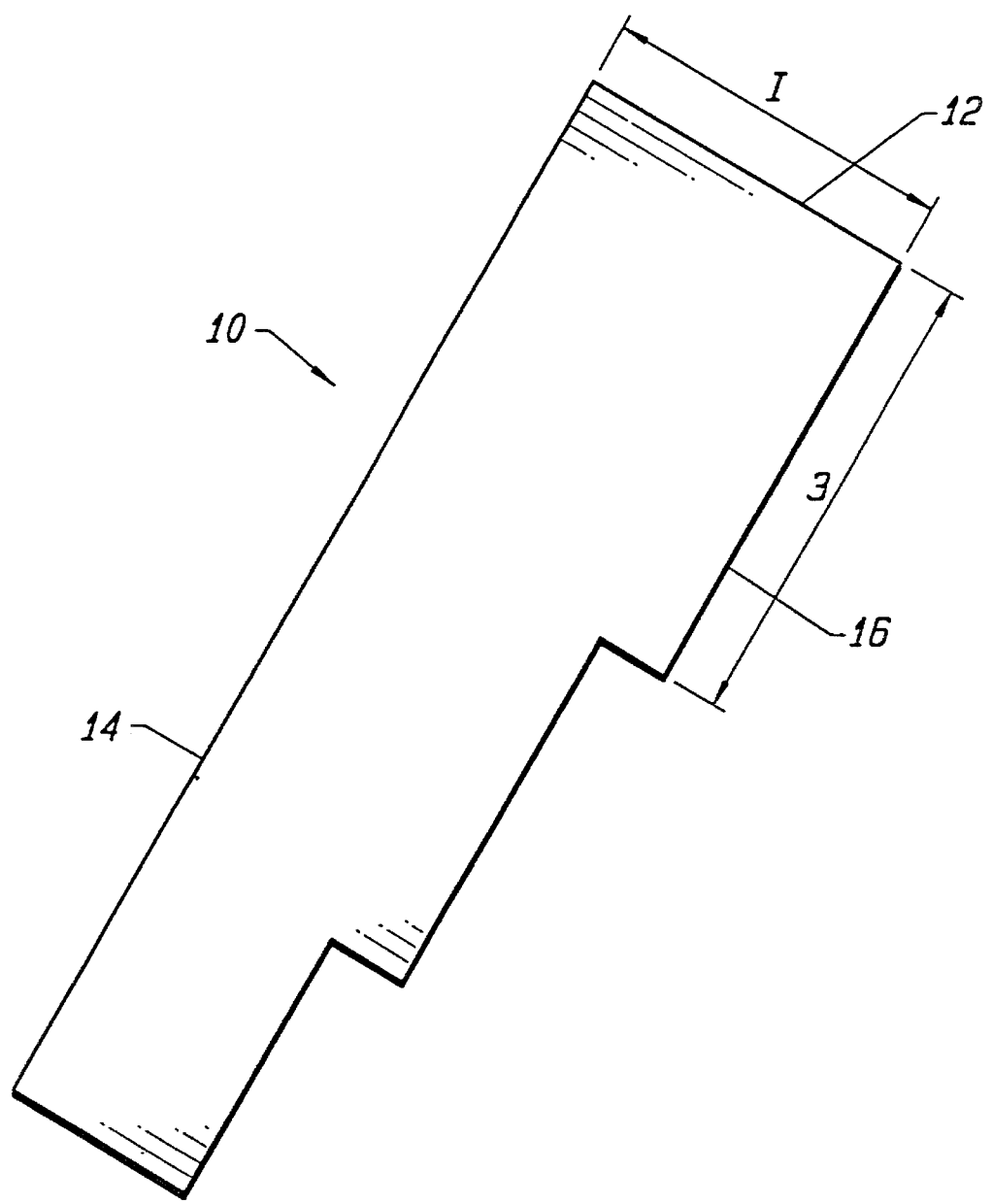
FIG. 1 is a plan view of the sizing template according to the present invention.

An exemplary embodiment of the sizing template 10 of the present invention is shown in FIG. 1. The sizing template 10 comprises a planar member 12 having a straight bottom edge 14 and a stepped top edge 16. Each step has a height H and a width W. The embodiment shown in FIG. 1 is designed particularly for use with orthogonal transdermal patches, such as the Nicotrol and Nicoderm nicotine patches.

Figure 2:
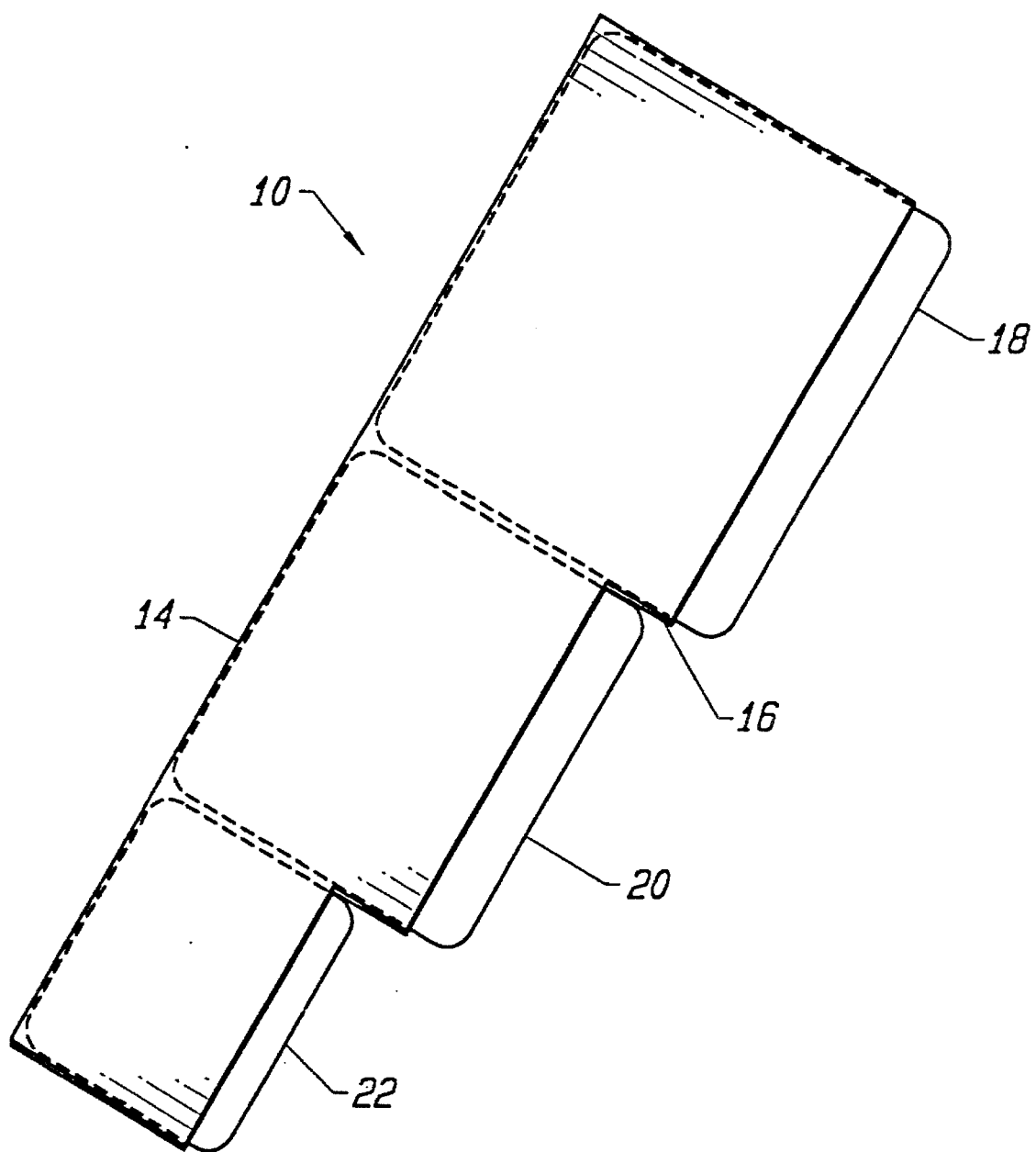
FIG. 2 is a plan view of the sizing template as in FIG. 1 with different sized transdermal patches being positioned on the template for marking and cutting.

As shown in FIG. 2, a typical nicotine transdermal patch, such as the Nicotrol® patch, has an orthogonal geometry and is available in a group of patches having different sizes and corresponding dosages. That is, the dosage is in direct proportion to the area of the patch. For example, the Nicotrol® transdermal patch system includes a group of three patches; namely, a 30 cm² patch 18, a 20 cm² patch 20, and a 10 cm² patch 22. The dimensions are 6.0 cm by 5.0 cm, 4.5 cm by 4.5 cm, and 3.4 cm by 3.0 cm, respectively. The sizing template 10 is configured so that each of the patches 18, 20, 22 has a dimension which corresponds to a location on the template which uniquely matches the dimension of each of the differently sized patches 18, 20, 22. More specifically, the width W of each step on the top edge 16 will uniquely match the width of one of the transdermal patches 18, 20, 22. The bottom edge 14 is straight to allow the bottom edge of each of the patches 18, 20, 22 to be aligned flush with the bottom edge 14 of the template 10. In this position, the top stepped edge 16 defines a line along which the patch is to be marked and/or cut to achieve the desired percentage of size reduction.

The present invention therefore allows a patient to simply and easily tailor the drug delivery as prescribed by a doctor. For example, the doctor may prescribe a specific dosage to the patient such that the patient would need 35 cm² of patch area. However, patch size availability may be limited to 30 cm², 20 cm² and 10 cm². Thus to obtain a dosage of 35 cm², at least one of the patches would need to be reduced in area and combined with another patch. For instance, a 30 cm² patch 18 could be used in connection with half of a 10 cm² patch 22. The present invention allows for such tailoring by providing a template 10 which facilitates reducing every size of transdermal patch, in this specific example, by 50%. Either the doctor or the patient could then simply uniquely match the 10 cm² patch 27 to the corresponding spot on the sizing template 10, and then mark and cut the patch 22 along the line defined by the top stepped edge 16.

The present invention also allows a patient to taper the drug delivery without having to purchase patches of a different size(s). For example, if a patient were currently using 50 cm² of patch area, and the doctor desired to reduce the dosage delivered by one-third, the required patch area would be 33 cm². However, no combination of existing patch sizes would allow for such an area. The present invention solves this problem by allowing for each patch to be proportionally reduced by the same size. Thus, if the patient were using a 30 cm² patch 18 and a 20 cm² patch 20 to meet the doctor's prescribed dosage of 50 cm², the 30 cm² patch 18 and the 20 cm² patch 20 could be placed on the unique spot on the sizing template 10 which is configured for a 33% size reduction and marked and cut to obtain the required area of 33 cm². In this manner, the patient can easily and effectively either taper or tailor the dosage as prescribed by the doctor.

The present invention can also allow a doctor to prescribe only one size of patch which may be reduced to any desired area (dosage), resulting in reduced complexity and/or costs to the patient. Typically, each size of patch requires a different prescription from the doctor, and the purchase of a combination of various sized patches can be expensive. With the present invention, costs may be reduced by prescribing only one size of patch along with the appropriate sizing template to meet the specified dosage given by the doctor.

The embodiment shown in FIGS. 1 and 2 can be configured to enable the transdermal patches to be reduced by any proportion. Typically, a patch will be reduced in area in the range from 10% to 90%. Also, the present invention is not limited to only having three steps as shown in FIGS. 1 and 2. Alternatively, the sizing template 10 may have as many steps as necessary to uniquely correspond with a number of different sized transdermal patches in a particular drug delivery system.

Figure 3:
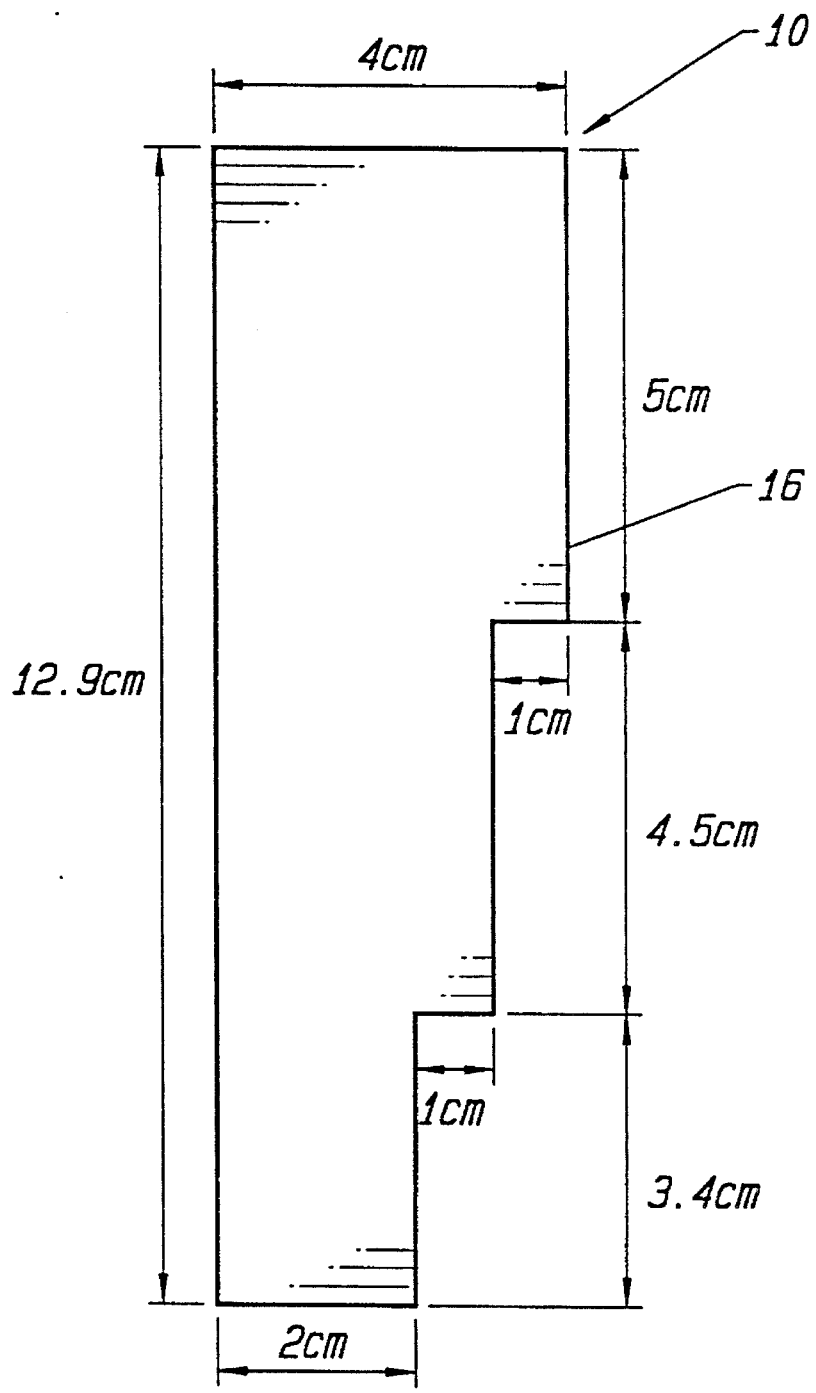
FIG. 3 is a plan view of a sizing template used with a system of patches having areas of 30 cm², 20 cm², and 10 cm² that are to be reduced in area by one-third.

Turning now to FIG. 3, the sizing template 10 which is configured to reduce the size of the transdermal patches 18, 20, 22, shown in FIG. 2, by approximately one-third is shown. The height of each stepped edge 16 is configured so that when a transdermal patch is placed on the unique position of the sizing template 10, the stepped edge 16 will define a line indicating where the patch should be cut to obtain a one-third size reduction in area. For example, the height of a typical 30 cm$^2$ patch is about 6 cm. The 30 cm$^2$ patch will correspond to the area on the template 10 having a height of 4 cm. The line defined by the top stepped edge 16 will then indicate where the patch should be cut to obtain a one-third reduction in size. The 20 cm$^2$ patch 20 and the 10 cm$^2$ patch 22 can be reduced in size in a manner similar to that just discussed in connection with the 30 cm$^2$ patch 18.

Numerous methods and devices may be used to mark and cut the transdermal patches. For instance, the template 10 can be placed over a transdermal patch which may then be placed on a rigid planar surface. A severing instrument, such as a sharp knife, can be translated across the patch along a line defined by the top stepped edge 16. Using this method, it will be desirable to construct the sizing template 10 with an appropriate thickness. Preferably, the thickness will be in the range from about 0.25 mm to 2 mm to allow the knife to easily follow the top stepped edge 16 when cutting the patch. However, the thickness of the template 10 is not limited to this specific range and will be dictated by the specific materials used to construct the template as well as the method of cutting the patches.

Another alternative way to mark and cut the patches is to use a marking instrument such as a pencil or pen to mark the patch along the line defined by the top stepped edge 16. The patch may then be moved away from the sizing template 10 and cut with a severing instrument, such as with scissors. Alternatively, the marking step may be avoided altogether by simply aligning a patch on the template 10 and using scissors to cut the patch along the top stepped edge 16.

The sizing template 10 will be constructed of any material that can be conformed to any shape similar to that shown in FIG. 1. Preferably, the template 10 will be constructed of a rigid or semi-rigid material such as polycarbonate, cardboard, card stock, plastic laminated cardstock, paper stock, plastics, metals, or the like, resulting in a template that is light-weight, portable, and easy to use as previously described.

The present invention is no way limited to having the steps of the sizing template 10 descend in the manner shown in FIG. 1. Alternatively, the steps may ascend or may be in any order as long as each position on the template 10 will uniquely define a position for each size of patch.

The present invention is not limited for use with orthogonal patches only. Alternatively, the invention can be adapted to any patch system having patches of defined geometries so that the area of the patches may be proportionally reduced by a template in the manner disclosed. As one example, the methods discussed in connection with this invention could also be used to reduce the size of elliptical patches. Instead of using a top stepped edge 16, a series of elliptical holes may be formed in the interior of a pre-marked transparent template to proportionally reduce the size of the elliptical patches.

Although the foregoing invention has been described in some detail by way of illustration and example, for purposes of clarity of understanding, it will be obvious that certain changes and modifications may be practiced within the scope of the appended claims.

What is claimed is:

1. A method for reducing the area of a transdermal patch, said method comprising:

aligning the patch at a location on a template which uniquely matches a dimension of the patch; and cutting the patch along a line defined by an edge of the template when the patch is at the aligned location.

2. A method as in claim 1, further comprising selecting the template from a group based on a desired percentage of area reduction.

3. The method of claim 2, wherein the desired percentage of area reduction is from 10 percent to 90 percent.

4. A method as in claim 1, further comprising marking the transdermal patch along the line prior to cutting.

5. The method of claim 1, wherein the patch is cut by translating a sharp instrument directly along the edge defined by the template.

6. A method for reducing the area of a transdermal patch which has an initial size selected from a group of sizes, said method comprising:

providing a template having a plurality of locations, wherein there is at least one location which uniquely matches a dimension of each of the sizes in the group;

aligning the patch at the location on the template which uniquely matches the dimension of the patch; and cutting the patch along a line defined by an edge of the template when the patch is at the aligned location.

7. A method as in claim 6, wherein the template is selected from a group of templates based on a desired percentage of area reduction.

8. The method of claim 7, wherein the desired percentage of area reduction is from 10 percent to 90 percent.

9. A method as in claim 6, further comprising marking the transdermal patch along the line prior to cutting.

10. The method of claim 6, wherein the patch is cut by translating a sharp instrument directly along the edge defined by the template.

* * * * *